(12) United States Patent
Kjaer et al.

(10) Patent No.: US 7,888,061 B2
(45) Date of Patent: Feb. 15, 2011

(54) METHOD OF STABILISING OR REACTIVATING A CREATININE SENSOR WITH A DIVALENT MANGANESE ION

(75) Inventors: Thomas Kjaer, Ballerup (DK); Jens Østergaard, Kgs. Lyngby (DK); Tina Kristensen, Struer (DK)

(73) Assignee: Radiometer Medical ApS, Bronshoj (DK)

( * ) Notice: Subject to any disclaimer, the term of this patent is extended or adjusted under 35 U.S.C. 154(b) by 811 days.

(21) Appl. No.: 11/434,251

(22) Filed: May 16, 2006

(65) Prior Publication Data

US 2006/0275860 A1 Dec. 7, 2006

Related U.S. Application Data

(60) Provisional application No. 60/697,360, filed on Jul. 8, 2005.

(51) Int. Cl.
- *C12Q 1/30* (2006.01)
- *C12Q 1/26* (2006.01)
- *C12M 1/34* (2006.01)

(52) U.S. Cl. .................. 435/27; 435/25; 435/287.1
(58) Field of Classification Search .................. None
See application file for complete search history.

(56) References Cited

U.S. PATENT DOCUMENTS

| | | | |
|---|---|---|---|
| 4,781,890 A | 11/1988 | Arai et al. | |
| 6,241,863 B1 | 6/2001 | Monbouquette | |
| 6,306,594 B1 * | 10/2001 | Cozzette et al. | 435/6 |
| 2002/0029964 A1 * | 3/2002 | Matsumoto | 204/403 |
| 2002/0090738 A1 * | 7/2002 | Cozzette et al. | 436/518 |
| 2003/0027239 A1 * | 2/2003 | Schaffar | 435/25 |

FOREIGN PATENT DOCUMENTS

| | | |
|---|---|---|
| EP | 0281000 | 9/1988 |
| EP | 0872728 | 10/1988 |
| EP | 1197749 | 4/2002 |
| WO | WO 2006/122553 | 11/2006 |
| WO | WO 2006/122554 | 11/2006 |

OTHER PUBLICATIONS

Database WPI Week 198647 Derwent Publications Ltd., London, GB; AN 1986-308698 XP002394933 & JP 61227799 A (Kobyashi Seiyaku) Oct. 9, 1986, Abstract.

Rikitake et al. "Creatinine Amidohydrolase (Creatininase) from *Pseudomonas putida*: Purification and Some Properties" J. Biochem 86(4): 1109-1117 (1979).

Inouye et al. "Purification and characterization of creatine amidinohydrolase of *Alcaligenes* origin" Chem Pharm Bull (Tokyo) 34(1):269-274 (1986).

Yoshimoto et al. "Crystal Structures of Creatininase Reveal the Substrate Binding Site and Provide an Insight into the Catalytic Mechanism" J. Mol. Biol. 337:399-416 (2004).

* cited by examiner

*Primary Examiner*—Lisa J Hobbs
(74) *Attorney, Agent, or Firm*—Morgan Lewis & Bockius LLP

(57) ABSTRACT

A method is provided for stabilizing a creatinine sensor comprising creatininase as a bioactive molecule. The creatininase is stabilised by exposing it to a sufficient amount of a divalent manganese ion. This result may be obtained by exposing the sensor to a solution comprising the divalent manganese ion or by introducing a composition within the sensor providing sustained release of the divalent manganese ion.

10 Claims, 5 Drawing Sheets

US 7,888,061 B2

METHOD OF STABILISING OR REACTIVATING A CREATININE SENSOR WITH A DIVALENT MANGANESE ION

RELATED APPLICATIONS

The present application claims the benefit of Danish application PA 2005/00718 (filed May 17, 2005) and U.S. provisional application 60/697,360 (filed Jul. 8, 2005), each of which is incorporated herein in its entirety by reference.

FIELD OF THE INVENTION

The present invention relates to a method of stabilising or reactivating a creatinine sensor comprising creatininase as a bioactive molecule, and a stabilised sensor and sensor membrane comprising creatininase as a bioactive molecule. The invention also relates to an apparatus for performing the method.

BACKGROUND OF THE INVENTION

Sensors for determining parameters in physiological samples are widely used in various fields of chemistry, biology and physiology. The presence and concentration of substances which are degradable by bioactive molecules, such as enzymes, may be determined using sensors comprising a suitable enzyme or enzymes. Such sensors are often referred to as biosensors. Biosensors employing both electrochemical and photometric principles are known.

The determination of creatinine in samples of physiological fluids, such as whole blood, serum or urine, is important for assessing renal function. Creatine phosphate is stored in the muscles of vertebrates and provides an energy reserve. It is irreversibly converted into creatinine (a degradation product) and the energy rich phosphate group. During normal muscle function about 1-2% per day of the total amount of creatine phosphate is converted into creatinine. Creatinine is released into the blood and removed by the kidneys. In a healthy individual the level of creatinine is thus relatively constant at about 35 to about 75 μM. If the level of creatinine in the blood increases it may be a sign of some malfunction of the kidneys. In such cases the level of creatinine may increase to levels as high as 2,000 μM.

Creatinine may be measured by biosensors comprising various enzymes, such as creatinine iminohydrolase (by detection of $NH_3$) or creatinine amidohydrolase. Creatinine amidohydrolase is also referred to as "creatininase".

In case of creatininase, the creatinine level in a physiological fluid is determined by a cascade of enzymatic reactions resulting in the formation of $H_2O_2$, which in turn may be detected amperometrically or photometrically. In some systems a further enzyme (e.g., peroxidase) or an indicator may be used (e.g., a luminophor).

The cascade of enzymatic reactions involving the enzymes creatininase (EC 3.5.2.10), creatine amidinohydrolase (EC 3.5.3.3—"creatinase") and sarcosine oxidase (EC 1.5.3.1) is represented by the following reactions:

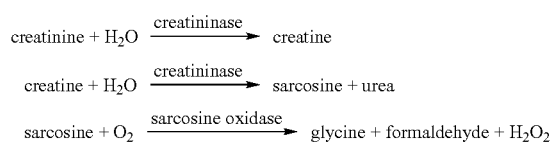

The intermediate product creatine is also present in samples of blood, serum or urine as such. Therefore, a dual sensor system is preferably employed if the creatinine is to be determined by the above cascade of enzymatic reactions. Using a dual sensor system the creatininase may be determined as the difference between the total of the two substances and the intermediate product alone. Accordingly, in a first sensor for the determination of the total concentration of creatinine and creatine in the sample, both creatininase, creatinase and sarcosine oxidase are present for converting creatinine and creatine into $H_2O_2$. In a second sensor for the determination of the concentration of creatine in the sample, creatinase and sarcosine oxidase are present for converting creatine into $H_2O_2$. The concentration of creatinine in the sample is thus determined from the difference between the total concentration of creatinine and creatine in the sample and the concentration of creatine in the sample.

Such a sensor system is disclosed in US published application 2004/0072277, which is derived from WO 02/14533 (Roche Diagnostics), published Feb. 21, 2002, wherein the $H_2O_2$ produced is detected amperometrically. The possible presence of enzyme inhibitors is discussed, particularly the inhibition of creatinase. A stable response of the dual sensor system is obtained for at least one week when measuring a sample of bovine serum containing about 90 μM creatinine.

The enzyme creatininase has been characterised in Kaoru Rikitake et al., "Creatinine Amidohydrolase (Creatininase) from Pseudomonas putida," J. Biochem. 1979, 86(4), pp. 1109-1117. Creatininase is a metalloenzyme carrying two zinc atoms in each subunit. It appears that the purified enzyme is very stable, especially after heat treatment, which is part of the purification process. Divalent metal ions of Mn, Co, Mg, Zn, Ni, Ca and Fe are shown to inhibit slightly the activity of the purified, heat-treated enzyme. In addition, creatininase shows only slight inhibition by ethylenediamine tetraacetic acid (EDTA) indicating that the zinc atoms are held firmly by the enzyme. This observation is also confirmed by the fact that the zinc ions may only be removed prior to the heat treatment of the enzyme and not from the heat-treated enzyme preparation. Upon removal of the zinc ions from creatininase by specific treatment of a cell digest, the resulting inactive apoenzyme is shown to be reactivated by addition of 0.5 mM of the divalent metal ions of Mn, Co, Mg, Zn, Ni or Fe. Similarly, Inouye et al., "Purification and Characterization of Creatinine Amidohydrolase of Alcaligenes Origin", Chem. Pharm. Bull. 34(1) 269-274 (1986), disclose that metal ion depleated creatininase can be reactivated by addition of a 1.0 mM $MnCl_2$ solution.

This characterisation of creatininase is confirmed in Tadashi Yoshimoto et al., "Crystal Structures of Creatininase Reveal the Substrate Binding Site and Provide an Insight into the Catalytic Mechanism," J. Mol. Biol. 2004, 337, pp. 399-416.

Thus, the enzyme creatininase is known to be a stable enzyme only slightly responsive to EDTA and other inhibitors.

Moreover, EP 0 872 728 A1 discloses a biosensor having a reaction layer comprising an enzyme and an electron acceptor, and having in the vicinity thereof a divalent water-soluble salt. The salts are preferably calcium salts, cadmium salts, manganese salts, magnesium salts or strontium salts; preferably chlorides, nitrates or sulfates. The minimum essential concentration of the metal for causing the metal to bind to the enzyme is described as 0.01 mg/mL corresponding to a minimum essential molar concentration of around 180 μM for manganese.

It has been found that when a dual sensor system of the above type is used for multiple measurements of creatinine in physiological samples, the response of the creatinine sensor starts to decrease after a certain period of time or a certain number of measurements. A gradual decrease in the sensitivity of the dual sensor system is the result. This decrease in sensitivity is a disadvantage, since it results in a short use life of the sensor system. Such sensors contain creatininase which is heat-treated, and as such, are expected to be insensitive to metal ion activation.

The relatively high concentrations of manganese apparently required for reactivating of metal-depleted enzyme (Rikitake et al. and Inouye et al.) or incorporation in a biosensor (EP 0 872 728 A1) will often be considered problematic, in particular when used in a multi-sensor apparatus. High concentrations in cleaning or rinse solutions may cause the precipitation of manganese salts, in particular if such solutions mix up with other solutions having different salt concentrations or pH values or with hypochlorite solutions. Moreover, the divalent manganese ion is an electroactive species which may cause unstable zero-currents in electrochemical sensors. Also, manganese may cause interference with magnesium sensors.

SUMMARY OF THE INVENTION

The present invention provides elegant solutions to the above-mentioned problems by means of a novel method and a novel creatinine sensor, a novel membrane for a creatinine sensor, and novel apparatuses for determining creatinine in a physiological fluid.

Hence, one aspect of the present invention relates to a method of stabilising or reactivating a creatinine sensor comprising creatininase as a bioactive molecule, comprising exposing the creatininase to an amount of a solution of a divalent manganese ion sufficient to increase the stability or to increase the activity of the sensor, wherein the divalent manganese ion is present in a concentration of in the range of about 0.01 to about 150 µM.

Another aspect of the present invention relates to a stabilised creatinine sensor comprising creatininase as a bioactive molecule, and a composition that releases an amount of a divalent manganese ion for a sustained period of time sufficient to stabilise or reactivate the sensor.

A third aspect of the present invention relates to a membrane for a creatinine sensor comprising creatininase as a bioactive molecule and a composition that releases an amount of a divalent manganese ion for a sustained period of time sufficient to stabilise or reactivate the sensor.

Further aspects of the present invention relate to (i) an apparatus for determining creatinine in a physiological fluid, comprising a creatinine sensor comprising creatininase as a bioactive molecule, a solution of a divalent manganese ion in a concentration of in the range of about 0.01 to about 150 µM, and a device for exposing the creatininase to the divalent manganese ion of the solution; (ii) an apparatus for determining creatinine in a physiological fluid, comprising a creatinine sensor comprising creatininase as a bioactive molecule, a filter comprising a composition that upon wetting releases a divalent manganese ion for a sustained period of time, a device for passing a suitable liquid over the filter to obtain a solution of a divalent manganese ion in a concentration of in the range of about 0.01 about 150 µM, and a device for exposing the creatininase to the divalent manganese ion of the solution; and (iii) an apparatus for determining creatinine in a physiological fluid, comprising a creatinine sensor comprising creatininase as a bioactive molecule, wherein the creatinine sensor is the sensor defined herein or a sensor comprising the membrane defined herein.

BRIEF DESCRIPTION OF THE DRAWINGS

The FIGS. below merely represent exemplary embodiments of the invention and are not in any way intended to limit the scope of the disclosure.

DETAILED DESCRIPTION OF THE INVENTION

Figure 1:
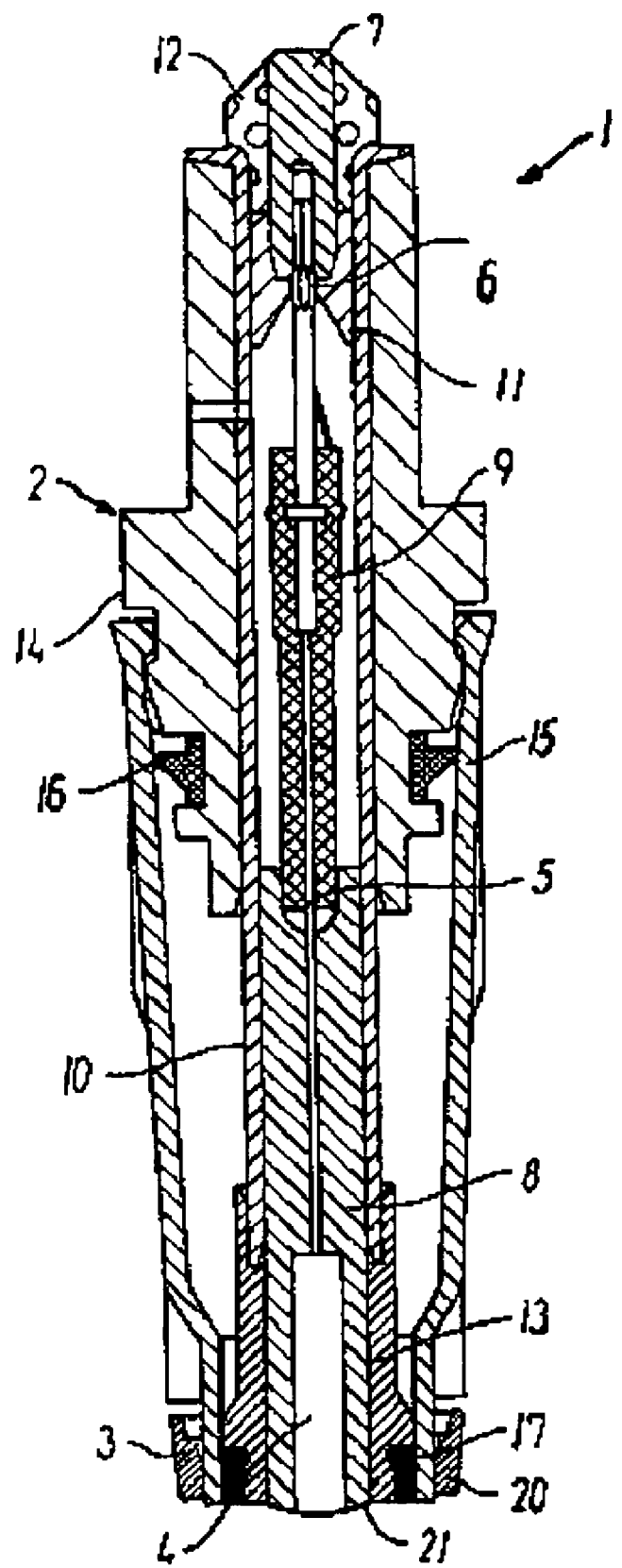
FIG. 1 illustrates an enzyme sensor comprising an electrode and a membrane.

An object of the invention is to provide a method of stabilising or reactivating a sensor comprising creatininase as a bioactive molecule.

Surprisingly, it has been found that this objective may be achieved by providing a method according to the invention, comprising exposing the creatininase to a low, but still sufficient amount of a divalent manganese ion.

A "sufficient amount" of a divalent manganese ion may be defined as an amount sufficient to influence the creatininase to increase the stability or activity of the sensor. There may be an upper limit to the amount of the divalent manganese ion having a beneficial effect on the sensor, for example, due to an inhibiting effect or other detrimental effects at higher concentrations. In an exemplary embodiment, the upper limit is about 150 µM. The workable ranges and the optimal level of the divalent manganese ion may be slightly influenced by the environment in which the method according to the invention is performed. In general, the higher the concentration of the divalent manganese ion, the higher the observed degree of stabilisation or reactivation, until the optimal level is reached, followed by possibly inhibitory concentrations.

A "sufficient amount" of a divalent manganese ion is the amount necessary to increase the stability or activity of the sensor. In an exemplary embodiment, a sufficient amount of manganese is at least about 0.01 µM. In another exemplary embodiment, a sufficient amount is at least about 0.1 µM. In another exemplary embodiment, a sufficient amount is at least about 1 µM. In yet another exemplary embodiment, a sufficient amount is at least about 2 µM.

In an exemplary embodiment, the level of the divalent manganese ion is at the most about 150 µM. In another embodiment, the level of the divalent manganese is at the most about 130 µM. In other embodiments, the level of the divalent manganese is at the most about 100 µM or, more typically, about 50 µM.

In various exemplary embodiments, the divalent manganese ion concentrations range from about 0.01 to about 150 µM; such as in the range of about 0.01 to about 130 µM; such as in the range of about 0.1 to about 100 µM; such as in the range of about 0.1 to about 50 µM; such as in the range of about 1 to about 50 µM; such as the range of about 2 to about 50 µM; or such as in the range of about 2 to about 25 µM.

As defined herein, "exposure" means a proximity sufficiently close to enable the desired interaction or effect of the divalent manganese ion on creatininase and may include actual contact between the interacting substances or something less.

Experiments with known creatinine sensors have shown that during use the creatinine sensor response to creatinine is declining whereas the creatinine sensor response to creatine is stable (relative sensor response, R). This observation indicates instability of the first enzyme in the reaction cascade, creatininase, despite its stable nature. The period of time after which the decline in relative sensor response starts depends on the initial excess in creatininase relative to the level of the other enzymes of the reaction cascade. The higher the excess, the longer time until the decline starts. However, when the concentration of enzyme is increased, the density and thus the diffusion resistance will increase resulting in a longer response time and a smaller signal. Therefore a low enzyme density is desirable to minimise response time. The period of time before the decline in relative sensor response starts is closely related to the overall lifetime of the sensor. According to the invention, an increased lifetime may be obtained without increasing the response time.

In fact, the divalent manganese ion has been observed to have a favourable effect on heat-treated creatininase in enzyme assays. This observation is in contrast to the observations made by Rikitake et al.

In an exemplary embodiment, the divalent manganese ion has, at concentrations in the range of about 0.01 to about 150 µM, proven to activate creatininase without having an adverse effect on the other enzymes of the dual sensor system for detecting creatinine or interfering with the measuring technique. This divalent manganese ion is thus suitable for use in the stabilisation or reactivation of sensors comprising creatininase as bioactive molecule.

Manganese has been observed not to deactivate typical sensor enzymes such as lactate oxidase, glucose oxidase and urease, hence, the divalent manganese ion is preferred for multi-analyte blood analysers.

It is also important that the divalent manganese ion is compatible with the various liquids to be conducted within the flow system, such as other parameters or components of the physiological sample, and does not precipitate within the flow system. It has been generally found that at the concentrations of about 0.01 to about 150 µM, the beneficial effects of the divalent manganese ion can be exploited while the risk of precipitation can be avoided.

It was discovered that when the creatinine sensor was exposed to the divalent manganese ion, a reactivation or stabilization of the sensor was observed.

Figure 3:
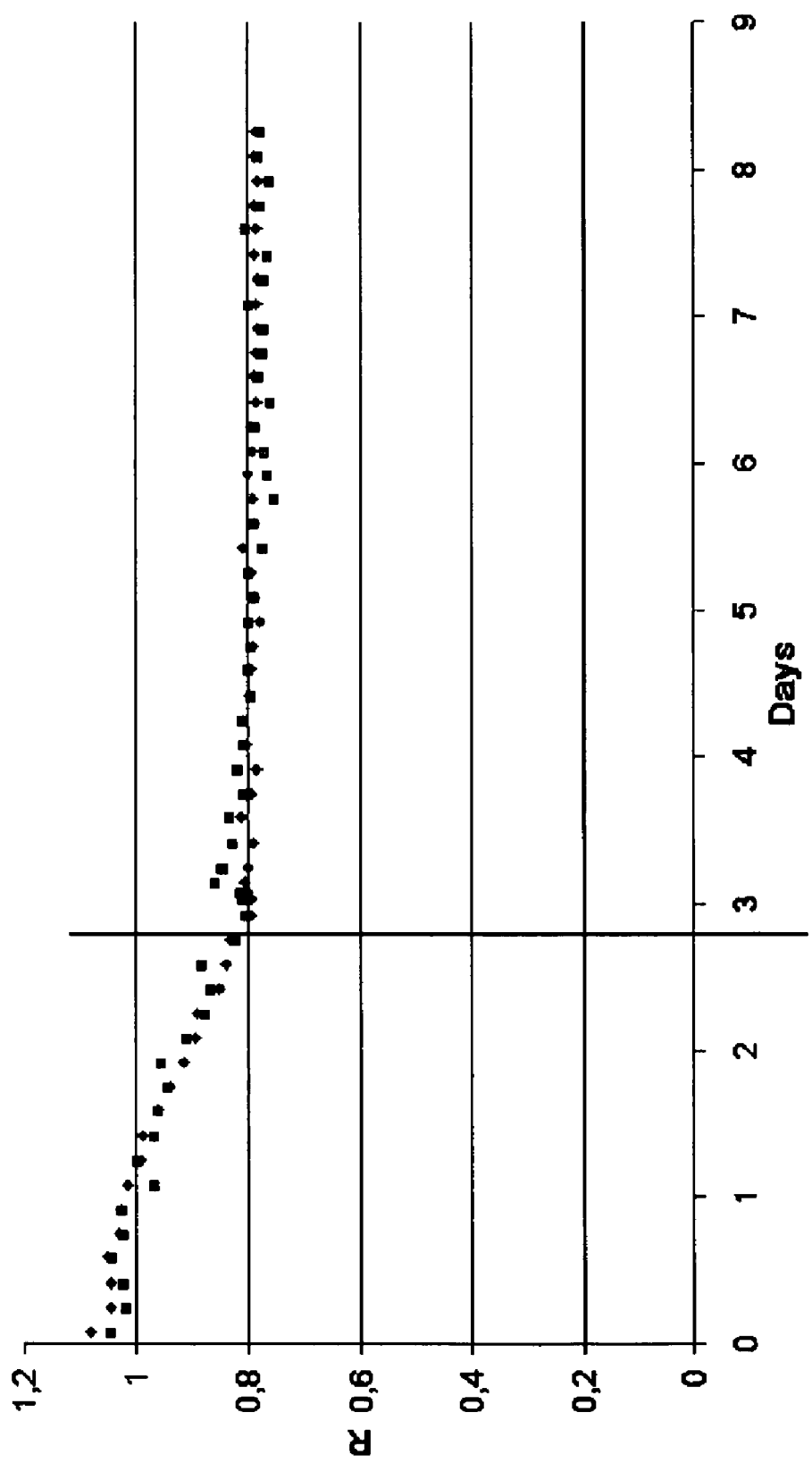
FIG. 3 compares the response of a creatinine sensor to creatinine to the response of the same sensor to creatine for a sensor with nearly no initial excess of creatininase.

As defined herein, the terms "stabilisation" and "stabilize" mean that an otherwise expected decrease in sensor response is avoided and that the sensor response is maintained at the sensor response level present immediately before exposure of the creatininase to the divalent manganese ion. Stabilisation is, e.g., observed in Example 1 and is illustrated in FIG. 3, where the sensor response level of approximately 0.8 was substantially maintained for at least 5 days by the continuous treatment with divalent manganese ions at a concentration of about 2 µM, whereas a decrease to less than about 0.5 would have been expected based on extrapolation from the first 2¾ days.

Figure 4:
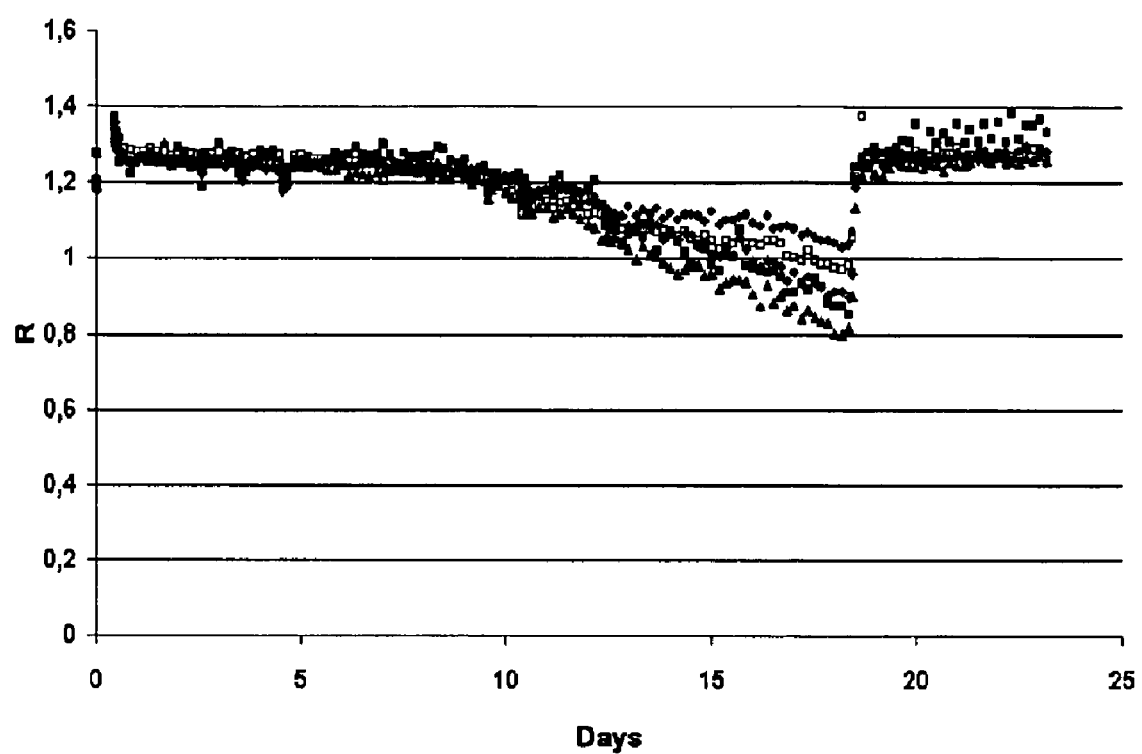
FIG. 4 compares the response of a creatinine sensor to creatinine to the response of the same sensor to creatine for a sensor with a significant excess of creatininase.

As defined herein, the terms "reactivation", "reactivate" and "activate" mean that an otherwise expected decrease in sensor response is avoided and that the sensor response is increased to a higher level than the sensor response level present immediately before exposure of the creatininase to the divalent manganese ion, and possibly up to the initial sensor response level. Reactivation was, e.g., observed in Example 1 and is illustrated in FIG. 4 where the sensor response level of approximately 0.9 (18 days) was increased to a level of approximately 1.3 (corresponding to the initial level) and maintained at this level for at least about 5 days by the continuous treatment with divalent manganese ions at a concentration of about 10 µM, whereas a decrease to less than about 0.8 would have been expected based on extrapolation from the first 18 days. Whether or not the initial level of the relative sensor response (R) is reached may depend on the initial excess of creatininase present relative to the other enzymes. Thus, if less than 100% of the creatininase is reactivated, the sensor response obtained after reactivation may be somewhat lower than the initial level if no significant excess of creatininase is employed.

The invention may be relevant for sensors of the conventional type or of the planar type, e.g., a thick-film sensor or a thin-film sensor. The enzyme membranes of such sensors are often layered structures and are referred to as layered membranes. Specific examples hereof are described in the Examples section.

In case of enzyme sensors of the conventional type, a membrane, e.g., a multi-layered membrane comprising, for example, a support layer, an enzyme layer, and a cover membrane, is typically assembled as a discrete object which is then arranged in conjunction with (i.e., generally mounted on the tip of) an electrode. See, e.g., FIGS. 1 and 2. Methods for the construction of such a multi-layered membrane are well-known in the art. See, e.g., WO 98/21356. Enzyme sensors of the conventional type may include track-etched membranes as well as solvent-cast membranes.

Figure 5:
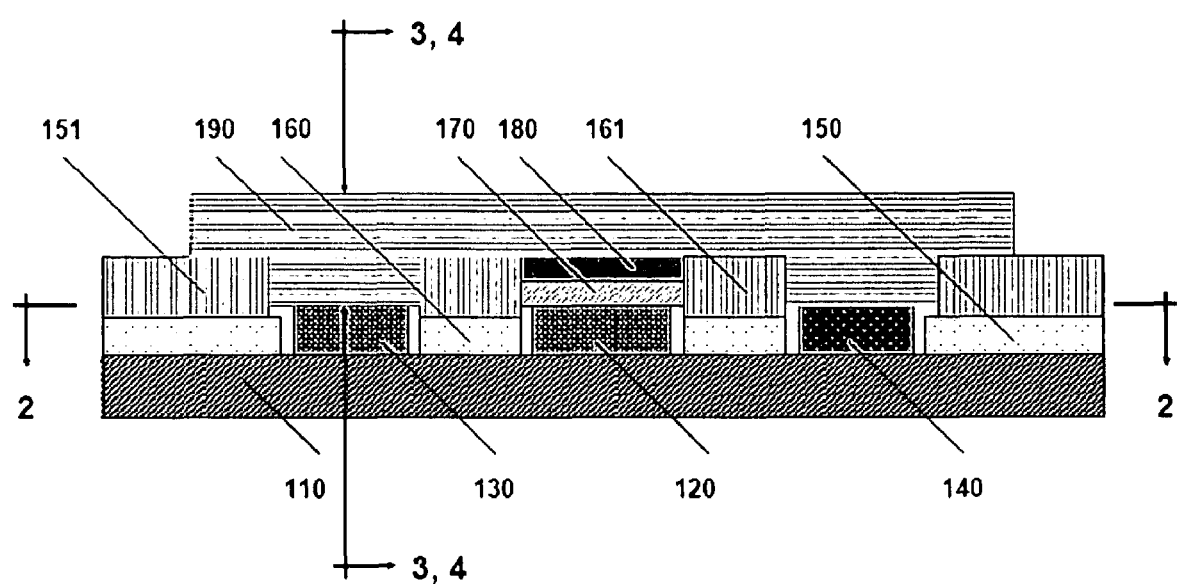
FIG. 5 illustrates a thick-film sensor.

In the case of enzyme sensors of the planar type, e.g., thick-film sensors and thin-film sensors, the electrode and the enzyme membrane comprising the enzyme layer and the cover membrane are arranged by depositing materials (typically sequentially and individually) corresponding to the electrode, any spacer layer and intermediate layer(s), the enzyme layer, and any cover membrane layer(s), on a solid, dielectric substrate, e.g., a ceramic or wafer material. An example of a planar sensor construction is illustrated in FIG. 5. Methods for the construction of planar type sensors, e.g., thick-film sensors and thin-film sensors, are well-known in the art. See, e.g., WO 01/90733, WO 01/65247 and WO 90/05910. The materials corresponding to the layers of such sensor membranes for planar sensors are most often deposited by solvent-casting.

The method of the invention will normally have most impact on a multi-use sensor, since such sensors are used for a longer time. Therefore the problem of deactivation is more important in these sensors.

A multi-use sensor is to be understood as a sensor which is used for more than one measurement and thus is exposed to more than one volume of sample and/or calibration solution.

Measurements of creatinine in samples of physiological fluids may take place in various automated and semi-automated analysers—many of which employ multiple sensors to measure multiple parameters. One example is a clinical analyser, particularly a blood analyser. The sample is introduced manually or automatically into a flow system of the analyser or into a flow system of a cassette for introduction into the analyser. Sensors for one or more parameters of the physiological sample may thus be exposed to the sample introduced into the flow system.

Another type of analyser is a flow injection analyser in which the sample of physiological fluid is introduced into a flowing stream that conveys the sample to a reaction zone and subsequently to a detection zone. In this case the sensor is to be understood as these zones including detector. To enable detection of creatininase in a physiological sample, the reaction zone could comprise creatininase, creatinase and sarcosine oxidase and in the detection zone $H_2O_2$ could be detected photometrically in the presence of an indicator, such as a luminophor or an enzyme, such as peroxidase.

In both types of analysers the sensors are normally exposed to the sample and other fluids that are conducted to and from the sensor.

A sufficient amount of the divalent manganese ion is preferably provided in a solution surrounding the creatininase, since it is expected that the divalent manganese ion is required to be present in dissolved form in order to sufficiently affect the creatininase. This result may generally be achieved in one of three ways, namely (i) by providing a pre-prepared solution of the divalent manganese ion, (ii) by preparing the solution of the divalent manganese ion in situ within the sensor, or (iii) by preparing the solution of the divalent manganese ion immediately before contact with the sensor. This will be explained in more detail in the following.

In a particular embodiment, a solution comprising the divalent manganese ion is conducted from a container to the sensor thus exposing the creatininase to the divalent manganese ion.

Such a solution may be prepared by dissolving a salt of the divalent manganese ion in an aqueous solution. Salts of the divalent manganese ion may include acetate, nitrate, sulphate and/or chloride salts. The counter ions of such salts are not expected to cause any detrimental effects in the sensors in the relevant concentrations.

Another object of the invention is to provide a stabilised creatinine sensor or a stabilising membrane for a creatinine sensor comprising creatininase as bioactive molecule. The sensor or membrane may further comprise a composition releasing a sufficient amount of a divalent manganese ion for a sustained period of time.

In this particular embodiment, the sensor comprises a composition that releases the divalent manganese ion for a sustained period of time when exposed to the sample or other suitable liquid. A sustained period of time is to be understood as a period which is sufficiently long to stabilise the activity of the creatininase until the end of the desired use life of the sensor. When the sensor is exposed to the sample or other suitable liquid, the manganese ion is released and brought into solution within the sensor, thus making the manganese ion available in the vicinity of the creatininase. After wetting of the sensor the creatininase is thus more or less continuously exposed to the divalent manganese ion. The composition is preferably present within the sensor membrane. Moreover, when the divalent manganese ion is released within the creatinine sensor, the risk of contamination and interference with other sensors in a multi-sensor apparatus can be almost completely avoided.

The composition releasing the divalent manganese ion for a sustained period of time when exposed to the sample or other suitable liquid may comprises the divalent manganese ion as a sparingly soluble salt. Examples of suitable sparingly soluble salts of the manganese ion include, but are not limited to, at least one of carbonate, citrate, tartrate, oxalate, orthophosphate, selenide, sulphide, hydroxide, oxalate, orthophosphate or selenite salts. Particular embodiments include carbonate, citrate and tartrate salts. It is believed that the most suitable salts can be selected based on knowledge about the solubility product of the salt in question taking into account the concentration of the counter ion (anion) in the solution into which the salt is to become dissolved (e.g., pH if the counter ion is $^-OH$). This is particularly relevant where the solution also servers other purposes, e.g., if the solution is simultaneously used as a rinse solution or a cleaning solution. As an example, the solubility product of manganese carbonate ($MnCO_3$) is about $2.2 \cdot 10^{-11}$ $M^2$. If the concentration of carbonate ($CO_3^{2-}$) ions in a suitable rinse solution is about $1.0 \cdot 10^{-6}$ M (1 µM), the concentration of the divalent manganese ion will be about $2.2 \cdot 10^{-5}$ M (22 µM) at saturation of the rinse solution with manganese carbonate.

Alternatively or additionally, the divalent manganese ion may be bound to an ion exchange resin providing sustained release.

Thus, the composition may also comprise a polymeric matrix that provides a sustained release of the divalent manganese ion. In this case the divalent manganese ion may be present as any of the above-mentioned salts or bound to the ion exchange resin. The release rate may thus be controlled both by the solubility of the salt and its binding by the ion exchange resin and polymeric matrix. Examples of suitable polymers include, but not limited to, ethylcellulose, methylcellulose, hydroxypropylmethylcellulose (HPMC), hydroxyethylcellulose (HEC), acrylic acid ester, cellulose acetate phthalate, HEC phthalate, HPMC phthalate or other cellulosic polymers, polyurethanes (PUR) or mixtures thereof.

In yet another embodiment of the invention, a filter is provided within the analyser, wherein the filter comprises the composition releasing the divalent manganese ion for a sustained period of time when exposed to the sample or other suitable liquid. The filter must be placed before the sensor, for example, in a cassette holding reference solutions for the apparatus. When a suitable liquid is passed over the filter a solution is provided within the flow system comprising the divalent manganese ion. This solution is then conducted to the sensor to expose the creatininase within the sensor to this solution. The choice of manganese salts for use in the filter will be as described hereinabove.

The solution for use in the first embodiment or the suitable liquid for use in the second and third embodiment may contain suitable buffers in order to provide a pH in the range of about 6 to about 9, preferably about 7 to about 7.5. Examples of suitable buffers include, but are not limited to, imidazole buffer, TRIS buffer or phosphate buffer.

The creatininase may be repeatedly or continuously exposed to the divalent manganese ion to obtain the stabilising or reactivating effect for an extended period of time.

As defined herein, the term "continuously" means that the sensor is exposed to a solution of the divalent manganese ion for at least about 80% of its operative lifetime. This is most conveniently realised by including the divalent manganese ion in a rinse solution and/or cleaning solution adapted for the sensor. As shown in Example 2, the inclusion of the divalent manganese ion in a rinse solution will effectively allow the sensor to become exposed to the divalent manganese ion for more than about 90% of its operative lifetime. Alternatively, a composition (or filter) comprising a sparingly soluble manganese(II) salt may also be used to obtain a continuous exposure.

As defined herein, the term "repeatedly" means that the sensor is exposed to a solution of the divalent manganese ion one or, preferably, several times during its operative lifetime. Preferably, the sensor is exposed at least about 3 times, such as at least about 5 times, or at least about 10 times, to a solution of the divalent manganese ion during its operative lifetime. The sensor may thus be exposed to the solution containing the divalent manganese ion continuously or in between measurements of samples of physiological fluids. The solution or the suitable liquid is preferably aqueous and may have other constituents, such as, for example, rinsing or cleaning agents and/or reference levels of parameters to be determined. Exemplary rinsing and/or cleaning agents include, but are not limited to, protein cleaving enzymes such as proteases, organic solvents and alkaline solvents. Exemplary parameters include pH; concentrations of electrolytes (e.g., $Li^+$, $Na^+$, $K^+$, $Ca^{2+}$, $Mg^{2+}$, $Cl^-$, $HCO_3^-$, $NH_3$ and $NH_4^+$); concentrations of other dissolved gases (e.g., oxygen and carbon dioxide), conventionally reported in the form of partial pressures, e.g., $PO_2$, $pCO_2$); hematocrit (Hct); concentration of haemoglobin and haemoglobin derivatives (e.g., oxyhaemoglobin, deoxyhaemoglobin, methaemoglobin, carboxyhaemoglobin, sulfhaemoglobin and fetal haemoglobin); and concentrations of metabolic factors (e.g., glucose, creatinine, creatine, urea (BUN), uric acid, lactic acid, pyruvic acid, ascorbic acid, phosphate, protein, bilirubin, cholesterol, triglycerides, phenylalanine and tyrosine). Such solutions containing the divalent manganese ion may serve several purposes at the same time in that the flow system and sensor surfaces may be cleaned and/or sensors calibrated while at the same time the creatinine sensor is stabilised or reactivated.

It is important to expose the creatininase to a sufficient amount of divalent manganese ion. In an exemplary embodiment, the solution surrounding the creatininase comprises the divalent manganese ion in a concentration in the range of about 0.01 to about 130 µM; such as, in the range of about 0.1 to about 100 µM; such as in the range of about 0.1 to about 50 µM.

In a particular embodiment, the concentration range of the divalent manganese ion depends on the frequency and duration of the exposure. If, for example, the creatininase is exposed to the solution for at least 50% of the time, the most preferred concentration would be about 5 to about 10 µM. Typically, if the exposure time is decreased, the concentration of the divalent manganese ion should be increased accordingly, however still keeping the concentration within the upper limit of about 150 µM.

It has been found that if, in addition to contact with a divalent manganese ion, the creatininase is exposed to a cation complexing agent, preferably at a concentration resulting in a binding of about half of the divalent manganese ion, the effective amount of the divalent manganese ion necessary to obtain a particular level of the stabilising or reactivating effect is lowered. In other words, the effect of a certain level of the divalent manganese ion is normally increased if a cation complexing agent is added. In a particular embodiment, the cation complexing agent is ethylenediamine tetraacetic acid (EDTA). EDTA binds the divalent manganese ion strongly and should preferably be added in a concentration of about half of the concentration of the divalent manganese ion. The advantage obtained by addition of a cation complexing agent resides in the ability of the cation complexing agent to efficiently bind any harmful cations (e.g., copper and mercury ions ($Cu^{2+}$, $Hg^{2+}$, etc.)) which may be present in the proximity of the sensor, e.g., contaminants occasioned by a prior sample. Because such harmful cations may only be present in very minute amounts (e.g., nanomolar or even pico molar amounts), the cation complexing agent added in, for example, micromolar amounts will bind virtually all such harmful cations and will in addition thereto bind a portion of the divalent manganese ions, leaving another portion of the divalent manganese ions available for interaction with the creatininase. If the cation complexing agent is added in a concentration resulting in a binding of nearly all of the divalent manganese ion, there would be an insufficient amount of unbound divalent manganese ions to expose to the creatininase. On the other hand, the presence of divalent manganese ions allows for the addition of the cation complexing agent without the risk of withdrawal of native divalent cations from the creatininase or other enzymes.

Accordingly, if the creatininase is exposed to the solution for at least about 50% of the time, a preferred concentration of the cation complexing agent would be in the range of about 1 to about 4 µM.

By employing the method according to the invention for stabilising or reactivating a sensor comprising creatininase as bioactive molecule, the lifetime of such a sensor may be extended from about one week to at least about one month or possibly up to two or three months. In fact the lifetime of the creatininase may be prolonged according to the method of the invention to such an extent that the lifetime of the creatinine sensor is limited by other factors than the lifetime of creatininase.

Further advantages of the method according to the invention are that a sensor is obtained which provides more precise and accurate measurements than those described in the prior art. As a consequence, fewer calibrations are necessary and fewer calibrations points are necessary.

In an amperometric dual sensor system for determining creatininase, the two exemplary sensors may comprise: creatininase, creatinase and sarcosine oxidase as bioactive molecules for detecting the total concentration of creatinine and creatine in the sample; and creatinase and sarcosine oxidase as bioactive molecules for detecting the concentration of creatine in the sample.

Both sensors amperometrically detect the end product, $H_2O_2$.

Although the present description, examples and claims are mainly focused on the use of a divalent manganese ion for stabilizing or reactivating a sensor comprising creatininase as bioactive molecule, it is envisaged that other divalent metal ions may be used in a corresponding manner, i.e., as it has been described for the divalent manganese ion. Examples of such alternative divalent metal ions include those selected from the group consisting of vanadium, chromium, iron, cobalt, nickel, zinc, as well as mixtures thereof.

EXAMPLES

The following examples are intended to illustrate the invention without limiting the invention. In all of the examples, creatininase from *Pseudomonas putida* was used, obtained from Roche Diagnostics, Mannheim, Germany.

Exemplary Sensor Construction (Conventional Sensor)

Each of the creatine and the creatinine sensors of the dual sensor system are built up as traditional amperometric sensors. FIG. 1 shows such a sensor 1, which is suited for mounting in an apparatus for measuring the concentration of analytes in a biological sample (e.g., an ABL™ 735 Blood Gas Analyzer (Radiometer Medical ApS, Copenhagen, Denmark)).

Basically, the sensor 1 comprises an electrode 2 onto which a membrane ring 3 is attached. The electrode 2 comprises a platinum anode 4 connected with a platinum wire 5, which, through a micro plug 6, is connected with a silver anode contact body 7. The platinum anode 4 and the lower part of the platinum wire 5 are sealed into a glass body 8. Between the glass body 8 and the micro plug 6, the platinum wire 5 is protected with heat-shrink tubing. A tubular silver reference electrode 10 encircles the upper part of the glass body 8 and extends the length of the electrode 2 to the anode contact body 7, which is fastened inside the reference electrode by means of a fixing body 11 and epoxy 12. The lower part of the glass body 8 is surrounded by an electrode base 13 whereto the membrane ring 3 is attached.

The upper part of the reference electrode 10 is surrounded by a plug part 14 for mounting the electrode 2 in the corresponding plug of an analysis apparatus (not shown) and for fixing a mantle 15. Gaskets 16 and 17 are placed between the electrode 2 and the mantle 15 in order to ensure that any electrolyte located at the measuring surface of the electrode 2 does not evaporate. The membrane ring 3, which is mounted at one end of the mantle 15, comprises a ring 20. A membrane 21 is stretched over the lower opening of the ring 20. This membrane 21 is shown in detail in FIG. 2.

Figure 2:
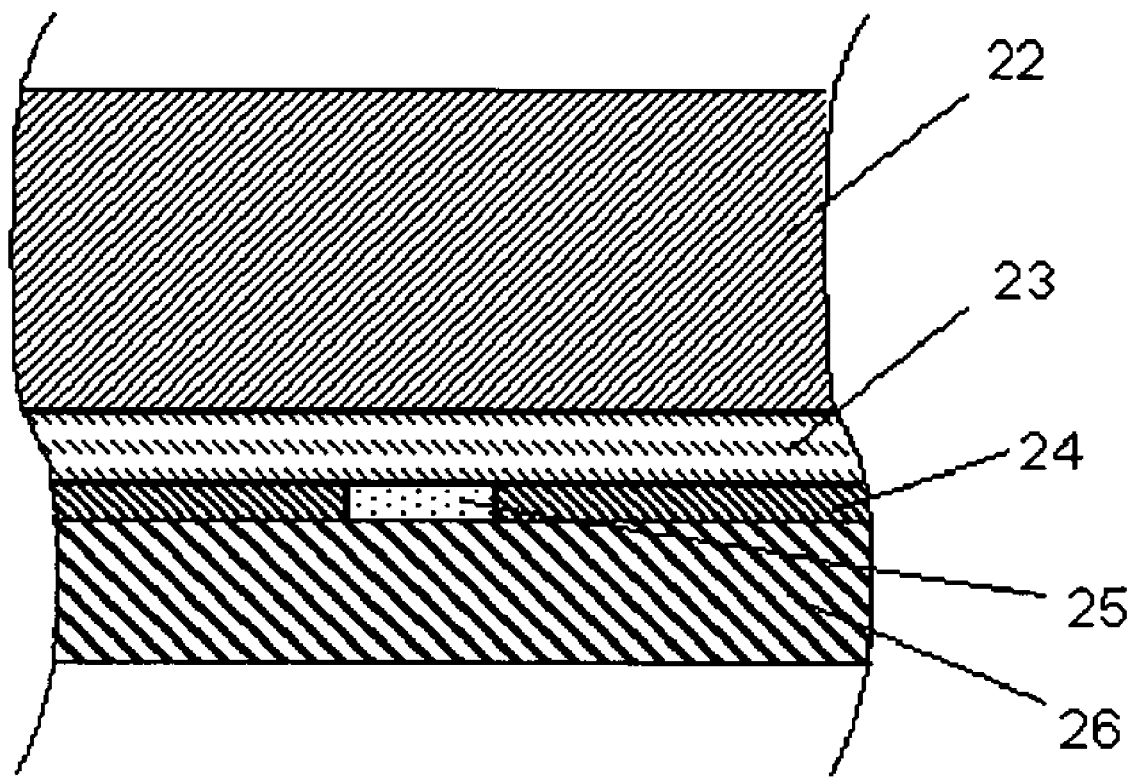
FIG. 2 illustrates in detail the membrane of the sensor of FIG. 1.

FIG. 2 shows details of the membrane 21 which comprises five layers: a noise reducing spacer layer 22 facing the platinum anode 4 of the electrode 2, an interference limiting membrane layer 23, a gasket 24 encircling an enzyme layer 25, and a diffusion limiting porous membrane layer 26 which has been coated with a hydrophilic protection layer of polyurethane having a water content of around 80%. The coated membrane layer 26 faces the sample to be analysed.

The noise reducing spacer layer 22 may be about a 21±2 μm track-edged membrane of polyethylene terephthalate (PETP). The interference limiting membrane layer 23 may be about a 6±2 μm porous membrane of cellulose acetate (CA).

The gasket 24 may be a 30±5 μm double sided adhesive disc having a center hole with a diameter of 1500 μm. The adhesive of the gasket 24 adheres to the interference limiting layer 23 and the diffusion limiting layer 26 to an extent that the enzymes are prevented from leaking out between the layers.

The enzyme layer 25 of the creatine sensor is typically an approximately 20 μm layer of creatinase and sarcosine oxidase crosslinked to glutaraldehyde mixed with suitable additives, such as buffer. The enzyme layer 25 of the creatinine sensor is typically an approximately 20 μm layer of creatininase, creatinase and sarcosine oxidase crosslinked to glutaraldehyde mixed with suitable additives, such as buffer.

The diffusion limiting porous membrane layer 26 may be an approximately 12 μm layer of polyethyleneterephthalate (PETP) (pore diameter approximately 0.1 μm; pore density approximately $3 \cdot 10^7$ pores/cm$^2$), which has been coated with a polyurethane having a water content of about 80%.

In the creatinine sensor, both creatine and creatinine are converted into hydrogen peroxide. In the creatine sensor, only creatine is converted into hydrogen peroxide.

At the amperometric electrode, hydrogen peroxide is oxidized anodically at +675 mV against Ag/AgCl. The resulting current flow is proportional to the creatinine/creatine concentration in the sample.

The concentration of creatinine is determined from the difference between the creatinine sensor signal (representing creatine+creatinine) and the creatine sensor signal (representing creatine).

Exemplary Sensor Construction (Thick-Film Sensor)

Each of the creatine and the creatinine sensors of the dual sensor system are built up as illustrated in FIG. 5.

Referring to FIG. 5, an alumina substrate 110 of a thickness of 200 μm is provided at one surface with a circular platinum working electrode 120 of a diameter 1000 μm and a thickness of 10 μm, an annular platinum counter electrode 130 of an outer diameter 3000 μm, an inner diameter 2000 μm and a thickness of 10 μm, covering the angular range 30-330° of the outer periphery of the working electrode, and a circular silver/silver chloride reference electrode 140 of a diameter 50 μm, positioned at the outer periphery of the working electrode at 0°. All of these three electrode structures are connected to the sensor electronics (not shown) across the alumina substrate 110 via platinum filed through holes (not shown) traversing the substrate. Upon operation, the working electrode 120 is polarised to +675 mV vs. the reference electrode 140.

Further on the alumina substrate 110 are two-layered structures of glass and polymer encapsulant. These two-layered structures include an annular structure 160, 161 of an outer diameter 1800 μm, an inner diameter 1200 μm and a thickness of 50 μm surrounding the working electrode 120 and a structure 150, 151 of a thickness 50 μm surrounding the complete electrode system. Both of these two-layered structures consist of an inner layer 150, 160 facing the alumina substrate 110 of ESL glass 4904 from ESL Europe of the United Kingdom of a thickness of 20 μm, and an outer layer 151, 161 of polymer encapsulant from SenDx Medical Inc. of California, USA as disclosed in international patent application WO97/43634 to SenDx Medical Inc. of California, USA which comprises 28.1% by weight of polyethylmethacrylate (Elvacite, part number 2041, from DuPont), 36.4% by weight of carbitol acetate, 34.3% by weight of silaninized kaolin (part number HF900 from Engelhard), 0.2% by weight of fumed silica and 1.0% by weight of trimethoxysilane.

A circular inner membrane 170 of cellulose acetate and cellulose acetate butyrate of a diameter 1200 μm and a thickness of 10 μm covers the working electrode 120.

For the creatinine sensor, a circular enzyme layer 180 of creatininase, creatinase and sarcosine oxidase crosslinked by glutaric aldehyde of a diameter 1200 μm and a thickness of 2 μm covers the inner membrane 170.

For the creatine sensor, a circular enzyme layer 180 of creatinase and sarcosine oxidase crosslinked by glutaric aldehyde of a diameter 1200 μm and a thickness of 2 μm covers the inner membrane 170.

The enzyme layer 180 was prepared by dispensing 0.4 μl of a buffered solution of the enzymes crosslinked by glutaric aldehyde on the cellulose acetate membrane 170. The enzyme layer was dried 30 min. at 37° C.

A circular outer membrane layer 190 of PVC/trimethyl-nonyl-triethylene glycol/diethylene glycol of a diameter 4000 μm and a thickness of 10 μm covers the complete electrode system, centered onto the working electrode 120.

The outer membrane was prepared from 1.35 gram of poly vinyl chloride (Aldrich 34,676-4), 0.0149 gram of trimethyl-nonyl-triethylene glycol (Tergitol TMN3 from Th. Goldschmidt) and 0.134 gram diethylene glycol which were added to 21.3 gram of tetrahydrofurane and 7.58 gram of cyclohexanone. The mixture was stirred until the PVC was dissolved and a homogenous solution was obtained. 28.5 gram of tetrahydrofurane was added to obtain a 2% solution of a 90/1/9 PVC/surfactant/hydrophilic compound composition. The solution was dispensed on the sensor area to cover all three electrodes and to have an approx. 0.5 mm overlap with the polymer encapsulant 151. The outer membranes were dried for 30 min. at 23±2° C. and for 1½ hour at 40° C.

All three layers 170, 180, 190 were dispensed on an x,y,z-table mounted with an automatic dispensing unit (IVEK pump).

In the creatinine sensor, both creatine and creatinine are converted into hydrogen peroxide. In the creatine sensor, only creatine is converted into hydrogen peroxide.

The concentration of creatinine is determined from the difference between the creatinine sensor signal (representing creatine+creatinine) and the creatine sensor signal (representing creatine).

Example 1

Influence of Manganese on Creatinine Sensor Measurements

A blood analyser of the type ABL™735 from Radiometer Medical ApS, Denmark, was modified to accommodate the dual sensor system described above ("Exemplary sensor construction (conventional sensor)").

Various concentrations of manganese were added to samples of the Radiometer Rinse Solution 54970. Manganese was added in the form of manganese(II) acetate to obtain concentrations of about 2 μM and 10 μM, respectively.

The stability of the creatinine sensor was tested by observing the sensor responses to calibration solutions containing each of the substrates creatinine and creatine.

The calibration solutions were prepared by dissolving about 200 μM creatinine in the Radiometer Calibration Solution 1 S1720 and about 200 μM creatine in the Radiometer Calibration Solution 2 S1730. These solutions were repeatedly introduced into the apparatus one after the other and sensor responses were obtained.

When introducing the solutions without any manganese, it was observed that the creatinine sensor response to creatinine was declining whereas the creatinine sensor response to creatine was stable. This observation indicated instability of creatininase, the first enzyme in the reaction cascade. Whether the decline in sensor response starts immediately or after a certain period of time depends on the initial excess in creatininase relative to creatinase and/or sarcosine oxidase. The higher the excess, the longer the time until the decline starts. However, if the enzyme density is too high, the undesirable result will be an increased diffusion resistance and thus a longer response time and smaller signal.

It is convenient to depict the relation between the creatinine sensor response to creatinine relative to the creatinine sensor response to creatine by the following ratio:

R=response to creatinine/response to creatine.

If R is constant, the creatininase activity is stable. A declining value for R indicates an overall loss of creatininase activity.

Two series of experiments were conducted.

In the first experiment, two sensors having nearly no initial excess of creatininase were exposed to the Rinse Solution (0 μM manganese(II) acetate) for 2¾ days. As shown in FIG. 3, R starts to decline shortly after initiation of the experiment. The sensors were subsequently exposed to the modified Rinse Solution (2 μM manganese(II) acetate) for 5½ days. The results (R values) are shown in FIG. 3. FIG. 3 shows that upon exposure of the sensor to a concentration of 2 μM of divalent manganese ions, the R value could be stabilized.

The same experiment as described above was conducted with five creatinine sensors having a significant initial excess of creatininase. In FIG. 4, R is depicted for this experiment. The sensors were tested on Rinse Solutions for 18 days that contain no manganese, upon which the sensors were reactivated by changing to Rinse Solutions containing 10 μM of manganese (10 μM manganese(II) acetate). As shown in FIG. 4, R started to decline after one week of testing. After 18 days, R had decreased from 1.3 to 0.9. Upon changing to the Rinse Solutions containing 10 μM of manganese after 18 days, the sensors were reactivated to obtain the initial level of R=1.3.

Example 2

Operation of a Creatinine Sensor

A blood analyser of the type ABL™ 837 from Radiometer Medical ApS, Denmark, was modified to accommodate the dual sensor system described above. The cleaning solution comprised a 10 μM concentration of divalent manganese ions. The sensor cleaning solution was also used form storing the sensor between measurements and calibrations.

The standard protocol for the apparatus include a one-point calibration (one calibration liquid) every four hours and a two-point calibration (two calibration liquids) every eight hours. Typically, about 40 measurements are conducted every day (24 hours).

When a calibration or sample measurement is conducted, the cleaning solution was removed from the sensors and the calibration liquid or the sample, respectively, was pumped to the sensors. The sample/liquid was allowed to stand for 30 sec. The calibration liquid or sample was then removed by means of a flush of the cleaning solution which was then allowed to stand at the sensors until the next calibration liquid or sample was introduced. The calibration liquid/sample was, thus, contacted with the sensors for a total of about 40 sec.

A "standard" working day involved 40 measurements and 3+2*3 (i.e., 9) calibrations. The measurements lasted for about at total of 1960 sec, i.e., about 33 min per working day. This means that the sensors were contacted with the cleaning solution for at least 97% of the time.

The foregoing detailed description has been given for clearness of understanding only and no unnecessary limitations should be understood therefrom as modifications will be obvious to those skilled in the art. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features herein before set forth and as follows in the scope of the appended claims.

The disclosures of each and every patent, patent application, and publication cited herein are hereby incorporated herein by reference in their entirety.

The invention claimed is:

1. A method of stabilising or reactivating a creatinine sensor comprising creatininase as a bioactive molecule, comprising exposing the creatininase to an amount of a solution of a divalent manganese ion sufficient to increase the stability or to increase the activity of the sensor,
   wherein the solution comprises the divalent manganese ion in a concentration of in the range of about 2 to about 10 μM,
   wherein the creatininase is exposed to the solution of the divalent manganese ion for at least about 50% of the time, and
   wherein the sensor is arranged in a multi-sensor array.

2. The method according to claim 1, wherein the creatininase is exposed to the amount of the divalent manganese ion by conveying the solution comprising the divalent manganese ion to the creatininase.

3. The method according to claim 1, wherein the solution is prepared by passing a suitable liquid over a filter comprising a composition that releases the divalent manganese ion for a sustained period of time prior to exposing the creatininase to the solution.

4. The method according to claim 1, wherein the amount of the divalent manganese ion is prepared as a solution by contacting a suitable liquid with a composition present within the sensor that releases the divalent manganese ion for a sustained period of time and then exposing the solution to the creatininase.

5. The method according to claim 3 or claim 4, wherein the composition comprises a sparingly soluble salt of the divalent manganese ion.

6. The method according to claim 5, wherein the sparingly soluble salt of the divalent manganese ion is selected from the group consisting of carbonate, citrate, tartrate, oxalate, orthophosphate, selenide, sulphide, hydroxide, oxalate, orthophosphate, selenite, and mixtures thereof.

7. The method according to claim 6, wherein the sparingly soluble salt is selected from the group consisting of carbonate, citrate, and tartrate.

8. The method according to claim 1, wherein the creatininase is further exposed to a solution comprising a cation complexing agent.

9. The method according to claim 8, wherein the cation complexing agent is ethylenediamine tetraacetic acid (EDTA).

10. The method according to claim 8 or claim 9, wherein the concentration of the cation complexing agent is in the range of about 1 to about 4 μM.

* * * * *